US012608802B2

(12) United States Patent
    Salehi et al.

(10) Patent No.:     US 12,608,802 B2
(45) Date of Patent:        Apr. 21, 2026

(54) PREDICTING EMBOLIZATION PROCEDURE STATUS

(71) Applicant: KONINKLIJKE PHILIPS N.V., Eindhoven (NL)

(72) Inventors: Leili Salehi, Waltham, MA (US); Ayushi Sinha, Baltimore, MD (US); Ramon Quido Erkamp, Swampscott, MA (US); Ashish Sattyavrat Panse, Burlington, MA (US); Grzegorz Andrzej Toporek, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 300 days.

(21) Appl. No.: 18/572,131

(22) PCT Filed: Jun. 21, 2022

(86) PCT No.: PCT/EP2022/066813
    § 371 (c)(1),
    (2) Date: Dec. 19, 2023

(87) PCT Pub. No.: WO2022/268767
    PCT Pub. Date: Dec. 29, 2022

(65) Prior Publication Data
    US 2024/0296557 A1     Sep. 5, 2024

Related U.S. Application Data

(60) Provisional application No. 63/214,418, filed on Jun. 24, 2021.

(30) Foreign Application Priority Data

Jul. 29, 2021     (EP) ..................................... 21188399

(51) Int. Cl.
    *G06T 7/00*         (2017.01)
    *A61B 5/02*         (2006.01)
    (Continued)

(52) U.S. Cl.
    CPC ........ *G06T 7/0012* (2013.01); *A61B 5/02014* (2013.01); *A61B 5/026* (2013.01);
    (Continued)

(58) Field of Classification Search
    CPC ......... G06T 7/0012; G06T 2207/10116; G06T 2207/20084; G06T 2207/30104;
    (Continued)

(56) References Cited

U.S. PATENT DOCUMENTS 10,537,282 B2 *   1/2020   Yamamori ........... A61B 5/0042
11,348,234 B2 *   5/2022   Segawa ............... A61B 5/0261
                (Continued)

FOREIGN PATENT DOCUMENTS

EP          4566528 A1 *   6/2025   ........... G06N 3/0464
JP       2020127672 A      8/2020
                (Continued)

OTHER PUBLICATIONS

Bhurwani et al., "Feasibility study for use of angiographic parametric imaging and deep neural networks for intracranial aneurysm occlusion prediction", J NeuroIntervent Surg., 2020, 12, pp. 714-719.

(Continued)

*Primary Examiner* — Scott A Rogers

(57)        ABSTRACT

A computer-implemented method of predicting a status of an embolization procedure on an aneurism, includes: receiving (S110) projection image data (110) representing temporal blood flow in a region of the anatomy including the aneurism during the embolization procedure; inputting (S120) the received projection image data (110) into a neural network (Continued)

(120) trained to predict temporal blood flow (130), wherein the neural network (120) is trained to predict temporal blood flow (130) using training data (140) representing temporal blood flow in a region of the anatomy that does not include an aneurism; and in response to the inputting (S120): generating (S130) an output (160) indicative of the status of the embolization procedure based on the predicted temporal blood flow.

16 Claims, 3 Drawing Sheets

(51) Int. Cl.
　　*A61B 5/026*　　　(2006.01)
　　*A61B 6/50*　　　(2024.01)
　　*A61B 18/00*　　　(2006.01)

(52) U.S. Cl.
　　CPC .... *A61B 6/504* (2013.01); *A61B 2018/00416* (2013.01); *G06T 2207/10116* (2013.01); *G06T 2207/20081* (2013.01); *G06T 2207/20084* (2013.01); *G06T 2207/30104* (2013.01)

(58) Field of Classification Search
　　CPC ..... A61B 5/02014; A61B 5/026; A61B 6/504; A61B 2018/00416
　　See application file for complete search history.

(56) References Cited

U.S. PATENT DOCUMENTS

| | | | | |
|---|---|---|---|---|
| 12,361,559 | B2 * | 7/2025 | Kim | A61B 6/504 |
| 2008/0192997 | A1 * | 8/2008 | Grass | G06T 11/008 |
| | | | | 382/128 |
| 2013/0345559 | A1 * | 12/2013 | Haemmerich | A61B 6/481 |
| | | | | 600/431 |
| 2015/0086093 | A1 * | 3/2015 | Fonte | A61B 5/0261 |
| | | | | 382/128 |
| 2017/0347966 | A1 * | 12/2017 | Yagi | G16H 50/50 |
| 2024/0050097 | A1 * | 2/2024 | Salehi | G16H 50/20 |
| 2025/0072971 | A1 * | 3/2025 | Jeong | A61B 34/10 |
| 2025/0078268 | A1 * | 3/2025 | Kim | G06T 7/0012 |

FOREIGN PATENT DOCUMENTS

| | | |
|---|---|---|
| WO | 2017017086 A1 | 2/2017 |
| WO | 2022129054 A1 | 6/2022 |

OTHER PUBLICATIONS

Bhurwani et al., Predicting treatment outcome of intracranial aneurysms using angiographic parametric imaging and recurrent neural networks, SPIEE Med. Imag., vol. 11314, (2020), pp. 113142O-113142O-10.

Ionita et al., Assessment of contrast flow modificaiton in aneurysms treated with closed-cell self-deploying asymmetric vascular stents (SAVS), Medical Imaging 2010: Biomedcial Applications in Molecular, Structural and Functional Imaging, Proc. of SPIE, vol. 7626, pp. 762601I-1-12.

Ionita et al., "Asymmetric vascular stent: Feasibility Study of a New Low-Porosity Patch-Containing Stent"., STROKE, vol. 39, No. 7, Apr. 24, 2008, pp. 2105-2113.

Mahdi et al., "Predicting treatment of outcome of intracranial aneurysms using angiographic parametric imaging and recurrent neural networks", Progress in Biomedical Optics and Imaging, SPIE, International Society for Optical Engineering , vol. 11314, Mar. 16, 2020, p. 113142O-1-10.

Health Quality Ontario, "Coil embolization for intracranial aneurysms: an evidence-based analysis", vol. 6, No. 1. (2006).

Ren et al., "Endovascular coiling of small intracranial aneurysms using a very soft bare platinum coil: A comparison of the packing performance of new and old HyperSoft® helical coils," Interv. Neuroradiol., vol. 22, No. 1, pp. 26-33, (2016).

Rehman et al., "An autopsy report of basilar artery aneurysm flow diversion complicated by postoperative day 3 hemorrhage from vessel rupture," BMJ Case Rep., vol. 11, No. 1, pp. 3-6, (2018).

Sadato et al., "Large residual volume, not low packing density, is the most influential risk factor for recanalization after coil embolization of cerebral aneurysms," PLoS One, vol. 11, No. 5, pp. 1-8, (2016).

Osanai et al., "Versatile Fill Coils: Initial Experience as Framing Coils for Oblong Aneurysms A Technical Case Report," pp. 287-294, (2014).

Wei et al., "A (Near) Real-Time Simulation Method of Aneurysm Coil Embolization," in Aneurysm, vol. 395, InTech, 2012, pp. 116-124.

Van Rooij et al., "Packing performance of GDC 360° coils in intracranial aneurysms: A comparison with complex orbit coils and helical GDC 10 coils," Am. J. Neuroradiol., vol. 28, No. 2, pp. 368-370, 2007.

Dong et al., "Progressive Cascaded Convolutional Neural Networks for Single Tree Detection with Google Earth Imagery," Remote Sens., 11(15).

https://radiologykey.com/22-the-basilar-tip/, downloaded Jan. 18, 2024.

July et al., Wahjoepramono and Springer Malaysia Representative Office, Neurovascular Surgery Surgical Approaches for Neurovascular Diseases. (2018).

International Search report and Written Opinion of PCT/EP2022/066813, dated Nov. 16, 2022.

* cited by examiner

PREDICTING EMBOLIZATION PROCEDURE STATUS

CROSS-REFERENCE TO PRIOR APPLICATIONS

This application is the U.S. National Phase application under 35 U.S.C. § 371 of International Application No. PCT/EP2022/066813, filed on Jun. 21, 2022, which claims the benefit of U.S. Provisional Patent Application Ser. No. 63/214,418, filed on Jun. 24, 2021, and European Patent Application No. 21188399.6, filed on Jul. 29, 2021. These applications are hereby incorporated by reference herein.

TECHNICAL FIELD

The present disclosure relates to predicting the status of an embolization procedure on an aneurism.

BACKGROUND

An aneurism is an unusually-enlarged region of a blood vessel. Aneurisms are caused by weaknesses in the blood vessel wall. Aneurisms can develop in any blood vessel in the body, and most frequently occur in the brain and in the abdominal aorta. Aneurisms require treatment in order to avoid the risk of rupture and consequent internal bleeding and/or haemorrhagic stroke.

Endovascular coil embolization is a common procedure for treating brain aneurisms because of its minimally invasive nature, and its low failure rate. Coil embolization starts with the insertion of framing coils. These are intended to fill the periphery of the aneurismal sac, stabilizing the structure for the subsequent insertion of filling coils. Filling coils are inserted after the framing coils. Filling coils are shorter and smaller than framing coils, and are packed inside the framing coils. Finally, finishing coils are inserted.

During treatment, is important that an aneurism is filled with the correct amount of coils. If an aneurism is under-filled with coils, there is a risk that the aneurism re-canalizes, and may consequently require further treatment. If an aneurism is over-filled with coils, there is a risk that the aneurism will rupture. Over-filling an aneurism with coils also incurs the risk that coils migrate out of the aneurism and into a parent vessel, thereby blocking blood flow in the parent vessel.

Various factors may be taken into account by a physician in order to fill an aneurism with the correct amount of coils. These include the coil packing density and the absolute residual volume. The coil packing density affects intra-aneurism hemodynamic flow. Using a high coil packing density reduces the risk that the aneurism re-canalizes. The absolute residual volume is a measure of the un-filled space in an aneurism and includes the space between loops of the coils. This factor is closely related to the packing density. If the packing density is low, there will be some residual volume that can facilitate re-canalization of the aneurism.

Coil embolization procedures are typically performed under X-ray imaging using a contrast agent. The progress of the procedure is assessed by injecting the contrast agent into a position upstream of the vessel, and imaging the contrast agent inside the aneurism from multiple angles. In so doing, a physician may estimate the amount of additional coils that need to be inserted in order to complete the coil embolization procedure.

However, as coils are inserted into the aneurism, newly-inserted coils obscure the visibility of previously-placed coils, as well as the aneurism itself. The inserted coils may for example fill the peripheral portion of the aneurism, and leave a hollow cavity in the middle which may not be recognized under x-ray imaging. This can lead to coil compaction and re-canalization of the aneurism after the embolization procedure.

Thus, as treatment progresses, it becomes increasingly difficult to observe the behavior and the distribution of the inserted coils on X-ray images. This makes it difficult to estimate the packing density and the residual volume within the aneurism. A physician may consequently try to obtain an improved estimate of the amount of additional coils that need to be inserted in order to complete the coil embolization procedure by imaging the contrast agent inside the aneurism from multiple angles. This, however provides limited additional information in the presence of such hollow cavities, and also increases the radiation dose to the patient.

Consequently, there is a need for improvements in determining the progress, or in other words the status, of embolization procedures.

SUMMARY

According to one aspect of the present disclosure, a computer-implemented method of predicting a status of an embolization procedure on an aneurism, is provided. The method includes:

receiving projection image data representing temporal blood flow in a region of the anatomy including the aneurism during the embolization procedure;

inputting the received projection image data into a neural network trained to predict temporal blood flow, wherein the neural network is trained to predict temporal blood flow using training data representing temporal blood flow in a region of the anatomy that does not include an aneurism; and in response to the inputting:

generating an output indicative of the status of the embolization procedure based on the predicted temporal blood flow.

Further aspects, features, and advantages of the present disclosure will become apparent from the following description of examples, which is made with reference to the accompanying drawings.

DETAILED DESCRIPTION

Figure 1:
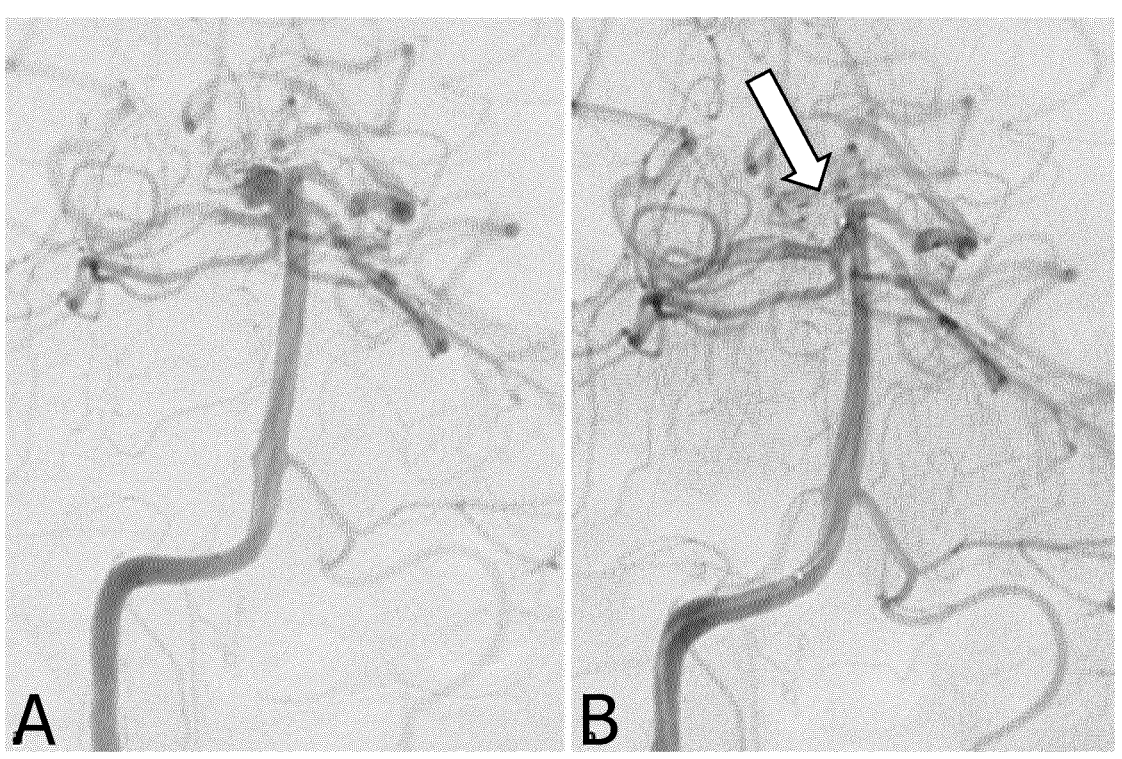
FIG. 1 illustrates a digital subtraction angiography image representing the cerebral vasculature (A) before and (B) after a coil embolization procedure.

Examples of the present disclosure are provided with reference to the following description and figures. In this description, for the purposes of explanation, numerous specific details of certain examples are set forth. Reference in the specification to "an example", "an implementation" or similar language means that a feature, structure, or characteristic described in connection with the example is included in at least that one example. It is also to be appreciated that features described in relation to one example may also be used in another example, and that all features are not necessarily duplicated in each example for the sake of brevity. For instance, features described in relation to a computer implemented method, may be implemented in a computer program product, and in a system, in a corresponding manner.

In the following description, reference is made to computer-implemented methods that involve predicting a status of an embolization procedure on an aneurism. Reference is made to examples in which the aneurism is in the brain. However, it is to be appreciated that the computer-implemented methods may be used to predict the status of an embolization procedure on aneurisms in other regions of the body than the brain, including in the heart, and for example in the abdominal aorta.

Reference is made herein to computer-implemented methods that involve predicting a status of a coil embolization procedure. It is, however, to be appreciated that methods may also be used to predict the status of embolization procedures that employ other strategies to treat an aneurism, including filling the aneurism with materials such as a gel or a glue.

Reference is made herein to computer-implemented methods that involve predicting a status of an embolization procedure on an aneurism using projection image data. The projection image data may in general be generated by an X-ray imaging system. In some examples, the projection image data is provided by digital subtraction angiography X-ray images. It is however to be appreciated that the projection image data may in general be provided by various types of X-ray images, including fluoroscopy images and contrast-enhanced X-ray images.

It is noted that the computer-implemented methods disclosed herein may be provided as a non-transitory computer-readable storage medium including computer-readable instructions stored thereon, which, when executed by at least one processor, cause the at least one processor to perform the method. In other words, the computer-implemented methods may be implemented in a computer program product. The computer program product can be provided by dedicated hardware, or hardware capable of running the software in association with appropriate software. When provided by a processor, the functions of the method features can be provided by a single dedicated processor, or by a single shared processor, or by a plurality of individual processors, some of which can be shared. The functions of one or more of the method features may for instance be provided by processors that are shared within a networked processing architecture such as a client/server architecture, the internet, or the cloud.

The explicit use of the terms "processor" or "controller" should not be interpreted as exclusively referring to hardware capable of running software, and can implicitly include, but is not limited to, digital signal processor "DSP" hardware, read only memory "ROM" for storing software, random access memory "RAM", a non-volatile storage device, and the like. Furthermore, examples of the present disclosure can take the form of a computer program product accessible from a computer-usable storage medium, or a computer-readable storage medium, the computer program product providing program code for use by or in connection with a computer or any instruction execution system. For the purposes of this description, a computer-usable storage medium or a computer readable storage medium can be any apparatus that can comprise, store, communicate, propagate, or transport a program for use by or in connection with an instruction execution system, apparatus, or device. The medium can be an electronic, magnetic, optical, electromagnetic, infrared, or a semiconductor system or device or propagation medium. Examples of computer-readable media include semiconductor or solid-state memories, magnetic tape, removable computer disks, random access memory "RAM", read-only memory "ROM", rigid magnetic disks and optical disks. Current examples of optical disks include compact disk-read only memory "CD-ROM", compact disk-read/write "CD-R/W", Blu-Ray™ and DVD.

As mentioned above, coil embolization procedures are typically performed under X-ray imaging using a contrast agent. The progress of the procedure is assessed by injecting the contrast agent into a position upstream of the vessel, and imaging the contrast agent inside the aneurism from multiple angles. In so doing, a physician may estimate the amount of additional coils that need to be inserted in order to complete the coil embolization procedure. However, as coils are inserted into the aneurism, newly-inserted coils obscure the visibility of previously-placed coils, as well as the aneurism itself. Consequently, as treatment progresses, it becomes increasingly difficult to observe the behavior and the distribution of the inserted coils on X-ray images.

By way of an example, FIG. 1 illustrates a digital subtraction angiography image representing the cerebral vasculature (A) before and (B) after a coil embolization procedure. In FIG. 1(A), the aneurism is seen as a large sac in dark contrast protruding outwards from the blood vessel. A physician may generate images such as FIG. 1A from multiple angles during a coil embolization procedure in order to visualize the blood filling and emptying from the aneurism over time. However, as mentioned above, as each of the coils is inserted into the aneurism, the coil mass obscures the visibility of the previously-placed coils, as well as the aneurism itself. Consequently, as treatment progresses, it becomes increasingly difficult to observe the behavior and the distribution of the inserted coils on X-ray images. Ultimately, when the aneurism has been filled with coils, there is negligible blood flow into the sac, as seen in FIG. 1(B) and the physician may deem the coil embolization procedure to be complete. As compared to FIG. 1(A), the DSA image illustrated in FIG. 1(B) is generated using an updated background image that includes the inserted coils, and therefore the original location of the aneurism is seen in light contrast in FIG. 1(B), indicating that there is negligible blood flow into the sac.

Figure 2:
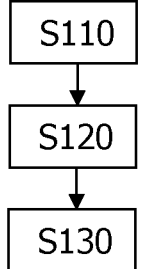
FIG. 2 is a flowchart illustrating a method of predicting a status of an embolization procedure on an aneurism, in accordance with some aspects of the present disclosure.

FIG. 2 is a flowchart illustrating a method of predicting a status of an embolization procedure on an aneurism, in accordance with some aspects of the present disclosure. With reference to FIG. 2, the method includes:

receiving S110 projection image data 110 representing temporal blood flow in a region of the anatomy including the aneurism during the embolization procedure;

inputting S120 the received projection image data 110 into a neural network 120 trained to predict temporal blood flow 130, wherein the neural network 120 is trained to predict temporal blood flow 130 using training data 140 representing temporal blood flow in a region of the anatomy that does not include an aneurism; and in response to the inputting S120:

generating S130 an output 160 indicative of the status of the embolization procedure.

The above method originates from the observation of a correlation between temporal blood flow through an aneurism, and how well filled the aneurism is with coils. Within the present context, the "temporal blood flow" refers to a blood flow through a vasculature over a certain period of time, as it can for example be determined via observing the contrast agent in a sequence of projection images such as DSA images. In particular, the temporal blood flow through the aneurism is of interest.

In the un-filled state, blood has been observed to enter an aneurism and to then arrive at the vasculature distal to the aneurism after a delay of a few heart cycles. As more coils are inserted into the aneurism, blood has been observed to arrive at the vasculature distal to the aneurism after a much shorter delay. Consequently, the temporal blood flow through an aneurism, can be used to determine how well filled the aneurism is with coils, or in other words, the status of the embolization procedure.

In the above method, the neural network predicts the temporal blood flow from the inputted projection data. Since the neural network was trained to predict temporal blood flow using training data representing temporal blood flow in a region of the anatomy that does not include an aneurism, which is assumed to be a region where a "normal", undisturbed blood flow exists, the temporal blood flow predicted by the neural network is its closest approximation to such "normal" blood flow, based on the inputted projection data.

At the start of an embolization procedure, the aneurism is un-filled with coils and the blood flow in the inputted projection data is expected to be ab-normal. It is expected to be ab-normal in the sense that the blood flow in the inputted projection data differs from the "normal" blood flow in the training data. In other words, at the start of the embolization procedure, the inputted projection data depicts a blood flow that is "out of distribution" relative to normal blood flow as represented by the training data. As the embolization procedure progresses and the aneurism is filled with coils, blood flow in the inputted projection data is expected to become closer to normal blood flow and thus become "in distribution" of the training data.

Various metrics that are based on these observations may be computed from the output of the neural network, and used independently or in combination, to generate the output 160 indicative of the status of the embolization procedure in the operation S130. These metrics are termed "out-of-distribution" metrics, and may be considered to represent the predicted blood flow in relation to the normal blood flow, in particular how close to "in distribution" the inputted projection data is relative to the training data. Accordingly, the operation of generating an output 160 indicative of the status of the embolization procedure, may be based on the computed value of the out-of-distribution metric 150.

In a first example, an out-of-distribution metric may be provided by the "normality" of the blood flow in the inputted projection image data, or in other words, a measure of the difference between the blood flow represented in the inputted projection image data 110 and the temporal blood flow in a region of the anatomy that does not include an aneurism 170 from the training data 140. As described above, as the embolization procedure progresses and the aneurism is filled with coils, blood flow in the inputted projection data is expected to become closer to normal blood flow.

In a second example, an out-of-distribution metric may be provided by the reconstruction error value. The reconstruction error value represents a difference between the predicted temporal blood flow 130 and the blood flow represented in the inputted projection image data 110. At the start of an embolization procedure, i.e. when the aneurism is un-filled with coils, the ab-normal blood flow in the inputted projection data is expected to result in the neural network making an inaccurate prediction of the blood flow. It is inaccurate in the sense that the predicted blood flow will not correspond well to the blood flow in the inputted projection data. This is because the neural network was trained to predict temporal blood flow using training data representing temporal blood flow in a region of the anatomy that does not include an aneurism. As the embolization procedure progresses and the aneurism is filled with coils, blood flow in the inputted projection data is expected to become closer to normal blood flow. Therefore, as the embolization procedure progresses, the reconstruction error value is expected to decrease.

In a third example an out-of-distribution metric may be provided by a confidence estimate. One way to generate a confidence estimate is to evaluate where the latent representation of the inputted projection image data lies within the distribution over the learned latent representations 170. At the start of the embolization procedure, the abnormal blood flow in the inputted projection data is expected to result in a latent representation that is far away from the mean of the distribution 170 (i.e., an outlier). As the embolization procedure progresses, blood flow in the inputted projection data is expected to become closer to normal blood flow and, therefore, result in latent representations closer to the mean of the distribution. This distance from the mean of the distribution may be used as a measure of confidence in the output of the trained network. Therefore, at the start of the procedure, the confidence is low, and as the procedure progresses, confidence is expected to increase.

In a fourth example, an out-of-distribution metric may be provided by using the neural network to generate an attention map. An attention map indicates the positions of features in the inputted projection image data 110 that have a dominant contribution to the predicted temporal blood flow 130. Attention maps derived from the encoder side of the network may indicate features that spatially overlap with the un-filled aneurism, since un-filled aneurisms are dominant features in projection images. However, since a decoder trained on projection images with "normal" blood flow is not expected to be able to reconstruct well from a latent represent of features associated with an aneurism, the accuracy of the predicted temporal blood flow is expected to be low. This situation may occur at the start of an embolization procedure when the neural network is inputted with projection images that include ab-normal blood flow. By contrast, if the attention map indicates features that are spatially distant from the aneurism, then the accuracy of the predicted temporal blood flow is expected to be high. This situation may occur towards the end of an embolization procedure when the neural network is inputted with projection images that include more normal blood flow and the aneurism is a less dominant or non-dominant feature in the images. Consequently, a measure of the difference between the positions of features indicated in the attention map, and a position of the aneurism in the inputted projection image data 110, may also provide an indicator of the status of the embolization procedure.

These four examples of out-of-distribution metrics, i.e. the difference between the blood flow represented in the inputted projection image data 110 and the temporal blood flow in a region of the anatomy that does not include an aneurism 170 from the training data 140; the reconstruction error value; the distance of the latent representation of the input projection image data from the mean of the learned distribution of latent representations; and the difference between the positions of features indicated in the attention map, and a position of the aneurism in the inputted projection image data 110, may therefore be used independently, or in combination, e.g. as a weighted sum, to compute a value of how close to "in distribution" the inputted projection data 110 is. The output 160 indicative of the status of the embolization procedure, may then be generated based on the computed value of how close to "in distribution" the inputted projection data is.

The method described above with reference to FIG. 2 is performed using the trained neural network 120, or in other words at inference time. The FIG. 2 method is described with further reference to FIG. 3, which is a schematic diagram illustrating (A) the training of a neural network 120 to predict temporal blood flow 130, and (B) the performance of inference with a neural network 120 trained to predict temporal blood flow 130, in accordance with some aspects of the present disclosure.

With reference to FIG. 2 and FIG. 3(B), in the operation S110, projection image data 110 is received. The projection image data 110 may be received from various sources, including a database, an imaging system, a computer readable storage medium, the internet, the cloud, and so forth. The projection image data 110 may be received via any form of data communication, including wired and wireless communication. By way of some examples, when wired communication is used, the communication may take place via an electrical or optical cable, and when wireless communication is used, the communication may for example be via RF or infrared signals.

As mentioned above, the projection image data 110 may be provided by an X-ray imaging system. The projection image data 110 may include a sequence of X-ray images. Thus, in FIG. 3(B), example projection image data 110 in the form of a sequence of X-ray images is received in the operation S110, and inputted into the trained neural network 120 in the operation S120. In FIG. 3(B) the X-ray images in the sequence represent temporal blood flow in the brain during an embolization procedure. More specifically, the X-ray images in the sequence include an example aneurism within the dashed outline and represent the blood flow in the aneurism during the embolization procedure. The aneurism is visible as a large sac in dark contrast within the dashed outline. In some examples, the projection image data 110 includes a representation of the temporal blood flow in one or more lumens upstream of the aneurism, and in one or more lumens downstream of the aneurism.

In general, the projection image data 110 may include a sequence of X-ray images that are generated instantaneously before being received, i.e. a live sequence of X-ray images, or the sequence of X-ray images may be have been generated some seconds, minutes, hours, or even days, or a longer period, beforehand. The sequence of X-ray images may be generated at time steps $t_{1 \ldots m}$, as illustrated in FIG. 3(B). The X-ray images may be generated following the injection of a contrast agent, and may therefore be referred-to as contrast-enhanced X-ray images. The contrast agent highlights the blood flow in the sequence of images. The contrast-enhanced X-ray images may for example include contrast-enhanced X-ray fluoroscopy images, or digital subtraction angiography "DSA" images. DSA images are generated by subtracting the image intensity values of an X-ray image that has been generated prior to the injection of a contrast agent into the vasculature, from corresponding positions in X-ray images that are generated after the contrast agent has been injected. In so doing, DSA images provide a visualization of the blood flow in the vasculature without background image features arising from dense materials such as bone.

In the operation S120, the received projection image data 110 is inputted into a trained neural network 120. By way of an example, FIG. 3(B) illustrates an example of a trained neural network 120 that includes a variational auto encoder "VAE" architecture, and which is suitable for this purpose. Further details on this example neural network architecture are provided below. Neural networks with alternative architectures to the example VAE illustrated in FIG. 3(B) may alternatively be used, including recurrent neural network "RNN", long short term memory "LSTM" architectures, and transformers.

The neural network 120 is trained to predict temporal blood flow 130 using training data 140 representing temporal blood flow in a region of the anatomy that does not include an aneurism. An example of predicted temporal blood flow 130 is illustrated in FIG. 3(B), and wherein the predicted temporal blood flow includes a sequence of images representing the predicted blood flow over time. In some examples the neural network may be trained using only training data 140 representing temporal blood flow in a region of the anatomy that does not include an aneurism.

The training data 140 may represent temporal blood flow in any region along the vasculature. By training the neural network using training data that does not include an aneurism, the neural network learns features associated with normal blood flow. At inference, when the trained neural network is inputted with data that includes an aneurism, the neural network 120 determines how much of an outlier the inputted data is to the learned distribution, and thus the extent to which normal blood flow has been restored. The training of the neural network 120 is described in more detail below with reference to FIG. 3(A).

With reference to FIG. 3(B), in response to inputting the received projection image data 110 into the neural network 120 in the operation S120, an output 160 indicative of the status of the embolization procedure, is then generated in the operation S130. As mentioned above, the output 160 indicating the status of the embolization procedure may be generated by the neural network based on the predicted blood flow and, in certain examples, on various out-of-distribution metrics being indicative of the predicted blood flow in relation to a normal blood flow. In certain examples, the value of an out-of-distribution metric 150 of the predicted temporal blood flow is computed, and the output 160 indicative of the status of the embolization procedure is generated based on the computed value of the out-of-distribution metric estimate 150, which value is indicative of the predicted temporal blood flow relative to a normal blood flow.

In one example, the status of the embolization procedure represents a proportion of the embolization procedure that has been completed. This is illustrated in FIG. 3(B) by the caption "% completed". The proportion of the embolization procedure that has been completed may for example be outputted as a numerical value, or alternatively as an icon, such as in the form of a pie chart. In another example, the status of the embolization procedure represents an expected time to complete the embolization procedure. The expected time to complete the embolization procedure may for example be outputted in the form of a numerical value, or as a progress bar indicating the lapsed duration of the procedure in relation to the expected time to complete the embolization procedure. The output 160 may also include a combination of these, and other, indications. In so doing, the output 160 provides an indication of the progress of the embolization without the need to repeatedly adjust the position of the imaging system in order to obtain images of the aneurism from multiple angles. Consequently, X-ray radiation dose to the patient may be reduced.

Figure 3:
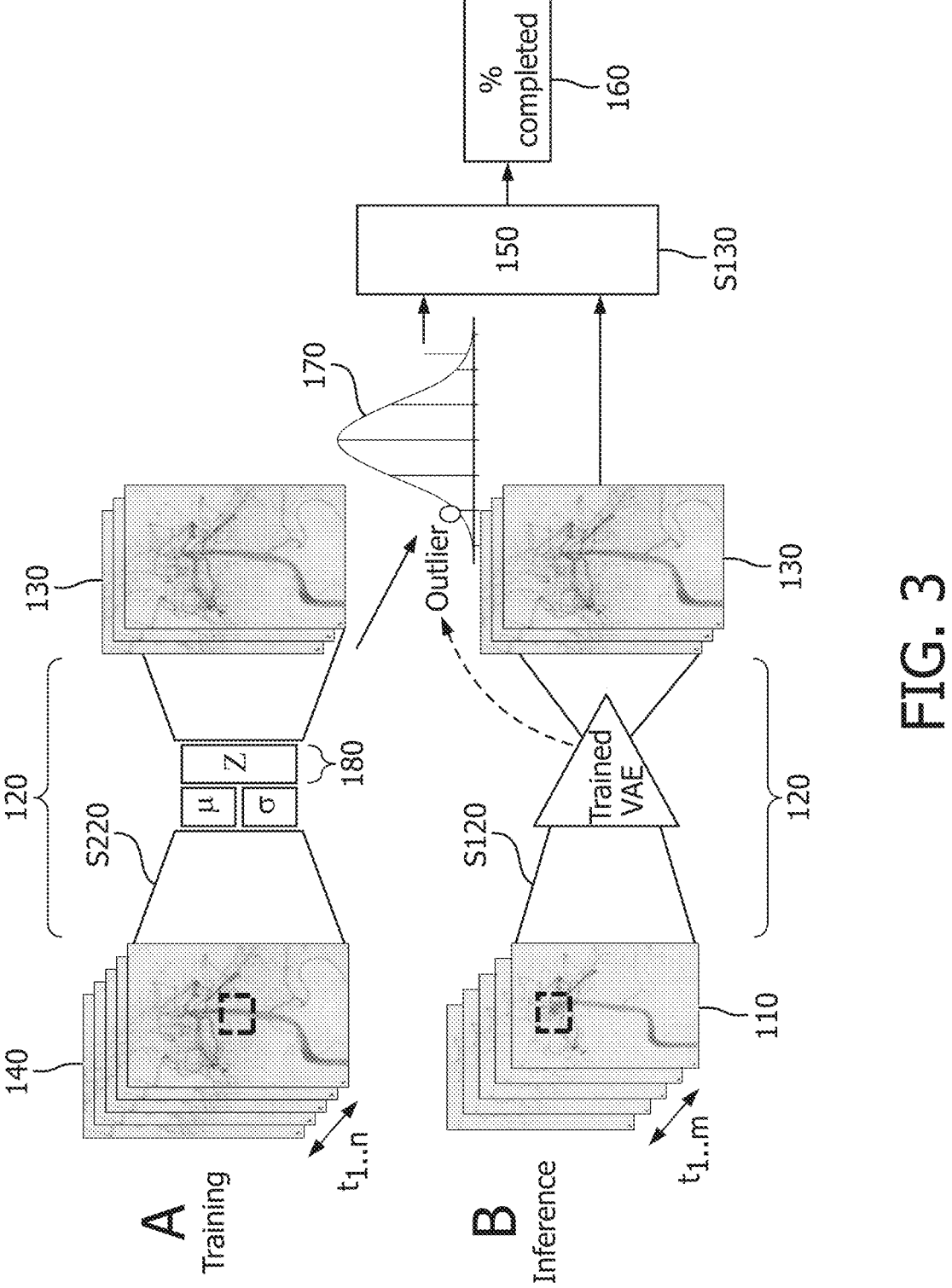
FIG. 3 is a schematic diagram illustrating (A) the training of a neural network 120 to predict temporal blood flow 130, and (B) the performance of inference with a neural network 120 trained to predict temporal blood flow 130, in accordance with some aspects of the present disclosure.

An example of the training of a neural network 120 to predict temporal blood flow is now described with reference to FIG. 3(A). In this example, reference is made to a neural network that includes a VAE architecture. In the example illustrated in FIG. 3(A), the encoder and decoder portions of the VAE may be provided by convolutional neural networks "CNNs" with three-dimensional inputs; i.e. two-dimensional projection images that are stacked in the time dimension, or alternatively by recurrent neural networks "RNNs" with a unidirectional or a bidirectional long short-term memory "LSTM" architecture. However, it is to be appreciated that neural networks with different architectures may alternatively be trained to predict temporal blood flow. During training, the neural network 120 illustrated in FIG. 3(A) learns a distribution, p, a, over the latent space, z, representing blood flow through a normally perfused vasculature. Alternative neural network to the example VAE illustrated in FIG. 3 that are also capable of learning an approximate distribution over the latent representation of the inputted training data 140, may also be trained in a similar manner.

During training, the VAE neural network 120 illustrated in FIG. 3A is inputted with training data 140 that includes multiple temporal sequences of images representing temporal blood flow in regions of the anatomy that do not include aneurisms. In general, the training data 140 may include temporal sequences of X-ray images. More specifically, the temporal sequences of X-ray images may include contrast-enhanced X-ray images such as contrast-enhanced X-ray fluoroscopy images, or digital subtraction angiography "DSA" images. In the example illustrated in FIG. 3(A), a single temporal sequence of DSA images is illustrated, and the inputted training data corresponds to the portion of the DSA images within the dashed outline in training data 140 at each of time steps $t_{1 \ldots m}$. Alternatively, the inputted training data may include complete X-ray images. During training, the inputted training data 140 may for example include a hundred or more of such temporal sequences. In general, the temporal sequences may be obtained from subjects that do not have any aneurism and/or patients that have undergone successful aneurism treatment procedures such as coil embolization, clipping, cap placement, and so forth, and in which the aneurism may be considered to be no longer present. The temporal sequences may be said to represent normally-perfused regions of the anatomy. The temporal sequences may represent blood flow in randomly-selected blood vessels in the X-ray images in the sequence.

During training, the VAE neural network 120 illustrated in FIG. 3(A) learns one or more vectors of latent variables 180 representing a distribution of blood flow. The vectors of latent variables 180 illustrated in FIG. 3(A) include a mean vector, m, and/or a variance vector, s. Since the inputted training data 140 represents normally-perfused blood flow, the mean and variance vectors represent a distribution of normally-perfused blood flow in the images in the inputted training data 140. The neural network 120 is trained to predict the temporal blood flow based on the learned one or more vectors of latent variables 180. In other words, during training, the VAE neural network 120 learns a distribution over the learned representation of the input sequences.

Consequently, the neural network 120 is able to generate a predicted temporal blood flow 130 from the vector(s) of latent variables 180.

In general, the training of a neural network involves inputting a large training dataset into the neural network, and iteratively adjusting the neural network's parameters until the trained neural network provides an accurate output. Training is often performed using a Graphics Processing Unit "GPU" or a dedicated neural processor such as a Neural Processing Unit "NPU" or a Tensor Processing Unit "TPU". Training often employs a centralized approach wherein cloud-based or mainframe-based neural processors are used to train a neural network. Following its training with the training dataset, the trained neural network may be deployed to a device for analyzing new input data during inference. The processing requirements during inference are significantly less than those required during training, allowing the neural network to be deployed to a variety of systems such as laptop computers, tablets, mobile phones and so forth. Inference may for example be performed by a Central Processing Unit "CPU", a GPU, an NPU, a TPU, on a server, or in the cloud.

The process of training the neural network 120 therefore includes adjusting its parameters. The parameters, or more particularly the weights and biases, control the operation of activation functions in the neural network. In supervised learning, the training process automatically adjusts the weights and the biases, such that when presented with the input data, the neural network accurately provides the corresponding expected output data. In order to do this, the value of the loss functions, or errors, are computed based on a difference between predicted output data and the expected output data. The value of the loss function may be computed using functions such as the negative log-likelihood loss, the mean squared error, or the Huber loss, or the cross entropy. During training, the value of the loss function is typically minimized, and training is terminated when the value of the loss function satisfies a stopping criterion. Sometimes, training is terminated when the value of the loss function satisfies one or more of multiple criteria.

Various methods are known for solving the loss minimization problem such as gradient descent, Quasi-Newton methods, and so forth. Various algorithms have been developed to implement these methods and their variants including but not limited to Stochastic Gradient Descent "SGD", batch gradient descent, mini-batch gradient descent, Gauss-Newton, Levenberg Marquardt, Momentum, Adam, Nadam, Adagrad, Adadelta, RMSProp, and Adamax "optimizers" These algorithms compute the derivative of the loss function with respect to the model parameters using the chain rule. This process is called backpropagation since derivatives are computed starting at the last layer or output layer, moving toward the first layer or input layer. These derivatives inform the algorithm how the model parameters must be adjusted in order to minimize the error function. That is, adjustments to model parameters are made starting from the output layer and working backwards in the network until the input layer is reached. In a first training iteration, the initial weights and biases are often randomized. The neural network then predicts the output data, which is likewise, random. Backpropagation is then used to adjust the weights and the biases. The training process is performed iteratively by making adjustments to the weights and biases in each iteration. Training is terminated when the error, or difference between the predicted output data and the expected output data, is within an acceptable range for the training data, or for some validation data. Subsequently the neural network may be deployed, and the trained neural network makes predictions on new input data using the trained values of its parameters. If the training process was successful, the trained neural network accurately predicts the expected output data from the new input data.

Figure 4:
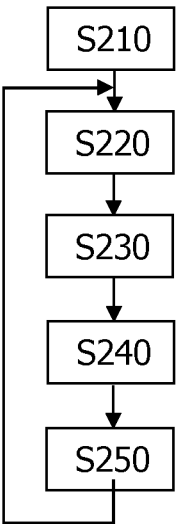
FIG. 4 is a flowchart illustrating a method of training a neural network to learn one or more vectors of latent variables representing a distribution of blood flow, in accordance with some aspects of the present disclosure.

FIG. 4 is a flowchart illustrating a method of training a neural network to learn one or more vectors of latent variables representing a distribution of blood flow, in accordance with some aspects of the present disclosure. The training method may be used to train the neural network illustrated in FIG. 3(A). With reference to FIG. 4 and FIG. 3(A), the neural network 120 is trained to learn the one or more vectors of latent variables 180 representing a distribution of blood flow by:

receiving S210 training data 140 comprising a plurality of temporal sequences of images, each temporal sequence including images representing blood flow at a plurality of time steps $t_{1 \ldots m}$ in a region of the anatomy that does not include an aneurism; and for each of a plurality of time steps $t_{1 \ldots m}$ in a temporal sequence:

inputting S220 into the neural network 120, the image corresponding to the time step $t_{1 \ldots m}$;

training S230 the neural network 120 to learn the one or more vectors of latent variables 180 representing the distribution of blood flow in the image at the time step $t_{1 \ldots m}$; sampling S240 from within the distribution of blood flow in the image represented by the one or more vectors of latent variables 180 to provide an expected blood flow at a subsequent time step $t_{1 \ldots m}$;

adjusting S250 parameters of the neural network 120 based on:

i) a value of a first loss function representing a difference between the probability distribution of the one or more vectors of latent variables 180, and reference probability distribution; and ii) a value of a second loss function representing a difference between the predicted blood flow 130 in the image at the subsequent time step $t_{1 \ldots m}$, and the blood flow in the input image from the training data 140 representing the blood flow at the subsequent time step $t_{1 \ldots m}$, until a stopping criterion is met; and repeating the inputting S220, the training S230, the sampling S240 and the adjusting S250 for each temporal sequence of images.

By way of an example, the value of the first loss function may for example be computed using the Kullback-Leibler "KL" divergence, which measures the difference between the probability distribution of the one or more vectors of latent variables 180 and a standard distribution. In this example, the reference probability distribution is therefore the standard distribution. The standard distribution that is used to compute the value of the first loss function may for example be a Gaussian or Normal distribution with mean equal to zero and variance equal to one. As an alternative to the standard distribution, the Dirichlet distribution may alternatively be used. Alternatives to the KL divergence include the Jensen-Shannon divergence, the Maximum-Mean Discrepancy, and so forth. The value of the second loss function may be computed using functions such as the L1 loss, or the mean squared error, or the Huber loss, or the structural similarity index loss, or the cross entropy.

In so doing, the neural network 120 is trained to predict temporal blood flow using training data from regions of the anatomy that do not include an aneurism. In other words, it is trained using blood flow from normally-perfused regions of the vasculature.

The trained neural network illustrated in FIG. 3(A) may then be used to perform inference. With reference to FIG. 3(B), during inference, projection data 110 representing temporal blood flow during the embolization procedure is inputted into the trained neural network 120. The trained neural network 120 then reconstructs its closest approximation to blood flow in a normally perfused region of the vasculature. Any inputted projection image data 110 that is not representative of the training data, i.e. inputted projection image data that does not correspond to a normally-perfused region, or in other words a completed embolization procedure, is an outlier to the learned distribution. A measure of how much of an outlier the inputted data is to the learned distribution, is then computed using one of the aforementioned out-of-distribution metrics, and used to indicate the status of the embolization procedure.

With reference to the VAE architecture in FIG. 3(B), since an autoencoder network reconstructs its inputted image, the representation of the input image, z, can be assigned a quality value. The value of the reconstruction error between the inputted and outputted images is a measure of this quality. The value of the reconstruction error may be computed using the value of the second loss function described above, and used as an indicator of how much of an outlier the inputted image is to normal blood flow, or in other words, serve as an out-of-distribution metric. The value of the reconstruction error may alternatively be used as the value of the confidence estimate of the predicted temporal blood flow 130, and thereby serve as another out-of-distribution metric.

Similarly, the value of the first loss function described above, i.e. the divergence value such as the Kullback-Leibler "KL" divergence value, can be computed and used as another out-of-distribution metric, in this case providing a measure of how close to "in distribution" the inputted image data is relative to the training data. More specifically, if the representation of an input sequence is an outlier to the learned distribution, then the representation may be an inlier in a different distribution with a different mean and standard deviation than the learned distribution. Since KL divergence is a measure of difference between two distributions, in this case, the KL divergence would be larger. If the representation of an input sequence is an inlier in the learned distribution, then the KL divergence is smaller. Alternatively, the mean difference between the representation of an input sequence and samples drawn from the trained distribution, can be used to indicate whether the input sequence is represented well by the learned encodings, in which case the difference is small, or if it is an outlier, in which case the difference is larger. Alternatively, the distance of the latent representation of an input sequence in terms of standard deviations away from the mean of the learned representation can also be used to indicate whether the input sequence is represented well by the learned encoding, in which case this distance is small (e.g., within one standard deviation), or if it is an outlier, in which case this distance is larger (e.g., greater than 2 standard deviations).

The reconstruction error value, the KL divergence value, and the location of the representation in the learned distribution can be used independently, or in combination, to provide the out-of-distribution metric 150, for example by combining their values as a weighted sum, since they each provide an estimate of how close to "in distribution" each inputted temporal sequence is.

At the start of an embolization procedure, the reconstruction error value, the KL divergence value, and the distance from mean of the latent representation of the input sequence are expected to be large since the blood flow in the inputted projection image data 110 will not closely represent the blood flow in a normally-perfused region. However, as the embolization procedure progresses, the reconstruction error value, the KL divergence value, and the distance value decrease as the blood flow becomes closer to normal blood flow. The reconstruction error value, the KL divergence value, and the distance value can therefore be used as indicators of the status of the embolization procedure.

In summary, in this example, the neural network 120 generates a reconstruction error value representing a difference between the predicted temporal blood flow 130 and the blood flow represented in the inputted projection image data 110 and/or a divergence value representing a difference between the probability distribution of the latent representation 180 of the inputted projection image data 110 and a reference probability distribution and/or a distance value representing the location of the latent representation of the inputted projection image data 110 relative to the mean of the learned latent representation; and the value of the out-of-distribution metric 150 is computed based on the reconstruction error value and/or the divergence value and/or the distance value.

The value(s) of the reconstruction error and/or KL divergence and/or distance can be used to compute the value of the out-of-distribution metric 150, and thereby indicate the status of the embolization procedure by comparing their values against a previously-determined relationship between the reconstruction error value and/or KL divergence value and/or distance value, and the status of the embolization procedure. The previously-determined relationship may be determined heuristically using a linear, or polynomial regression, for example. Alternatively, the value(s) of the reconstruction error and/or KL divergence can be inputted into a further neural network that is trained to establish a relationship between these values and the status of the embolization procedure. In this latter example, the status of the embolization procedure may be provided by this further neural network. A relationship between these values and the status of the embolization procedure may alternatively be established using other machine learning techniques. Alternatively, the predicted temporal blood flow 130 and the blood flow represented in the inputted projection image data 110 can also be directly inputted into a neural network to regress a relationship between a similarity between the inputted and predicted image data and the status of the embolization procedure.

In another example, as an alternative to, or in addition to using the reconstruction error value and/or KL divergence value and/or distance value to compute the value of the out-of-distribution metric 150, the neural network 120 may generate an attention map, and a value of the out-of-distribution metric 150 is determined using the attention map. An attention map indicates the positions of features in the inputted projection image data 110 that have a dominant contribution to the predicted blood flow. If the positions of the features in the attention map coincide with, for example, vasculature distal to the aneurism, then the value of the out-of-distribution metric 150 is high. By contrast, if the positions of the features in the attention map coincide with the position of the aneurism, then the value of the out-of-distribution metric 150 is low since this indicates that the attention of the network is around a single location and, therefore, the representation of this image does not encode enough information of surrounding vasculature to accurately reconstruct surrounding vasculature. In this example, the neural network 120 generates an attention map indicating a position of one or more features in the inputted projection image data 110 having a dominant contribution to the predicted temporal blood flow 130. Furthermore, the value of the out-of-distribution metric 150 is computed based on a difference between the position of the one or more features indicated in the attention map, and a position of the aneurism in the inputted projection image data 110.

In one example, at inference time, the method may also include generating an output indicative of an expected clinical outcome of the embolization procedure at a future point in time. This output may be generated based on the reconstruction error value and/or the (KL) divergence values obtained from the neural network throughout the embolization procedure. The output may for example represent the expected clinical outcome at a follow-up interval of six or eighteen months, for example. By way of an example, if insufficient coil is inserted into the aneurism during an embolization procedure, the expected clinical outcome at the six- or eighteen-month follow-up time is coil compaction or re-canalization of the aneurism. This clinical outcome manifests itself in the reconstruction error value and/or the (KL) divergence values of the neural network throughout the embolization procedure because the blood flow through the aneurism will be slower than normal and there is still residual volume remaining in the aneurism. Similarly, if too much coil was inserted during the embolization procedure, the expected clinical outcome at the six- or eighteen-month follow-up time is coil migration into the parent vessel, or aneurism rupture. This behavior can also manifest itself in the reconstruction error value and/or (KL) divergence value. In this case, the reconstruction error value and/or (KL) divergence value may reach a "100% completed" threshold and remains at that level for multiple DSA sequence acquisitions as embolization procedure continues. Consequently, by comparing the reconstruction error value and/or KL divergence values generated by the neural network throughout an embolization procedure to the values obtained from different clinical procedures and their respective outcomes, these values can be used to predict the clinical outcome of the embolization procedure at a future point in time. The association may be provided heuristically using linear or polynomial regression, a neural network, or another machine learning technique.

In one example, at inference time, a simulation of the blood flow in the region of the anatomy in the absence of the aneurism is also used to generate the output 160 indicative of the status of the embolization procedure in the operation S130. In this example, volumetric image data that includes the aneurism, is acquired. The volumetric image data may be CT data, or MRI data, for example. The volumetric image data is acquired prior to the embolization procedure. The volumetric image data is segmented in order to provide a model of the region of the anatomy. The model is then adapted in order to provide a model of the region of the anatomy in the absence of the aneurism, A simulation of the blood flow in the region of the anatomy in the absence of the aneurism, is then generated using the adapted model. The predicted temporal blood flow that is predicted by the neural network 120 is then compared with the simulated blood flow in the absence of the aneurism in order to determine the status, for example the percentage completion, of the embolization procedure. In this example, at inference time, the method includes:

receiving volumetric image data corresponding to the region of the anatomy in the received projection image data 110, the volumetric image data being generated prior to commencement of the embolization procedure;

simulating, based on a segmentation of the volumetric image data, a blood flow in the region of the anatomy in the absence of the aneurism; and wherein the generating S130 an output 160 indicative of the status of the embolization procedure, is determined based further on a comparison between the simulated blood flow in the region of the anatomy in the absence of the aneurism, and the predicted temporal blood flow predicted by the neural network 120.

In this example, the completion of the embolization procedure may be indicated when the difference between the simulated blood flow and the corresponding blood flow in the inputted projection image data 110 is below a predetermined threshold, as well as the values of the reconstruction error and/or the (KL) divergence, meet one or more criteria. Alternatively, the completion of the embolization procedure may be indicated when the difference between the simulated blood flow and the corresponding predicted temporal blood flow 130 that is predicted by the neural network 120 is below a predetermined threshold, as well as the values of the reconstruction error and/or the KL divergence, meet one or more criteria.

In one example, patient data may also be inputted into the neural network 120 at inference time and used to predict the status of the embolization procedure. In this example, the neural network 120 is trained to predict the status of an embolization procedure based further on the patient data, and the inference-time method further includes:

receiving patient data relating to the aneurism;

inputting the received patient data into the neural network 120; and predicting the status of the embolization procedure based further on the patient data.

The patient data may for example include one or more of: a computed aneurism volume, patient age, smoking history, genomic data, and so forth. In so doing, a more accurate prediction of the status may be provided.

In one example, the inference-time method may include identifying the aneurism in the received projection image data 110 prior to the inputting S120 the received projection image data 110 into the neural network 120. The aneurism may be identified manually, or automatically. Thus, the operation of identifying the aneurism may include: i) receiving user input indicative of a region of interest in the received projection image data 110 that includes the aneurism; or ii) automatically identifying the aneurism in the received projection image data 110.

When the identification is performed manually, a user interface may be provided for allowing a user to define a region of interest in the projection image data using a mouse, a joystick, a touchscreen, or another user input device. The user interface may for example define the region of interest by changing the shape of a bounding box.

When the identification is performed automatically, the aneurism may be identified using known techniques such as thresholding, region growing, template matching, level sets, active contour modelling, neural networks, e.g. U-Nets, and so forth.

Blood vessels that are proximal and distal to the aneurism may also be identified automatically in the projection image data based on the time at which contrast agent enters or leaves the aneurism in the image.

In one example, the user interface permits a user to identify areas in the projection image data 110 that are to be blocked- or zeroed-out prior to inputting the projection image data into the neural network 120. The user interface may for example include a mouse, a joystick, a touchscreen, or another user input device that allows a user to define such areas in the projection image data. This allows a user to remove potentially confounding regions from the projection image data. Confounding regions might for example include features such as additional aneurisms, plaque, an implanted device, and so forth that could otherwise affect blood flow through the projection image data 110 that is inputted into the neural network. The user interface may likewise permit a user to identify such regions in the training data 140 prior to the use of the training data to train the neural network. The inputted training data 140 may also be augmented to include zeroed-out regions that are randomly selected, or selected such that blocked-out regions mimic actual areas that may need to be blocked out, for example based on expert annotations.

In one example, the positions of confounding regions is detected automatically in the projection image data 110 and/or in the training data 140. In this example, if blood flow shows no change, or insufficient change during the embolization procedure, a warning may be provided to notify a user. This may alert the user to the fact that there is another cause for the slow blood flow, such as a further aneurism, plaque, and so forth. This allows the user to limit their reliance on the neural network, and to consider to use an alternative solution to indicate the progress of the embolization procedure. A neural network that identifies the positions of aneurisms in the projection image data may be used for this purpose.

Electronic health record "EHR" data may also be used to identify factors that may increase the chances of the presence of confounding regions. Factors such as blood pressure, body mass index "BMI", cardiac health, smoking history, family health history, treatment history, and so forth can be collected during inference, and used to learn an association between the factor(s) and reconstruction error and/or divergence values during the embolization procedure and the presence of one or more confounding regions. For example, a high BMI value may indicate a higher likelihood of the presence of plaque, while smoking history may indicate higher likelihood of the presence of other aneurisms due to weakened vessel walls, both of which can slow down contrast flow in the global vasculature images. This association may be learned via linear/polynomial regression, neural networks, or other machine learning techniques.

In one example, at inference time, the method may also include outputting the aforementioned attention map. Outputting the attention map may provide a user with confidence in the predictions of the neural network 120. For example, if the features in the attention map do not coincide with the target aneurism, then a user's confidence of the system may be low, allowing the user to limit their reliance on the system. The attention of the neural network may be justifiably focused away from a target aneurism if there are additional aneurisms or plaques in other regions within the inputted projection image data, and in which case the attention map may be focused on these other regions. In this case a user may, via the aforementioned user interface, block-out or zero-out the other regions in the projection image data prior to inputting the projection image data into the neural network 120. The neural network may consequently focus on the target aneurism and output an accurate status of the embolization procedure. However, if these other regions include blood vessels that are near to the target aneurism and such blocking is not possible, then a warning may be outputted indicating this mismatch between the location of the target aneurism and the network's attention. The user may over-ride the warning if the user observes that re-canalization immediately proximal to the target aneurysm is occurring as expected and a slowdown in blood flow is occurring further along the vasculature due to another aneurysm or plaque, etc. The method may also include outputting a recommendation to a user to change an orientation of the imaging system if a particular view contains too many confounding factors that cannot be blocked out.

In another example, a system for predicting a status of an embolization procedure on an aneurism, is provided. The system comprises one or more processors configured to:

receive S110 projection image data 110 representing temporal blood flow in a region of the anatomy including the aneurism during the embolization procedure;

input S120 the received projection image data 110 into a neural network 120 trained to predict temporal blood flow 130, wherein the neural network 120 is trained to predict temporal blood flow 130 using training data 140 representing temporal blood flow in a region of the anatomy that does not include an aneurism; and to in response to the input S120:

generate S130 an output 160 indicative of the status of the embolization procedure.

The system may also implement one or more of the operations described in relation to the above-described methods. The system may also include an imaging system for providing the projection image data 110.

The above examples are to be understood as illustrative of the present disclosure, and not restrictive. Further examples are also contemplated. For instance, the examples described in relation to computer-implemented methods, may also be provided by the computer program product, or by the computer-readable storage medium, or by the system in a corresponding manner. It is to be understood that a feature described in relation to any one example may be used alone, or in combination with other described features, and may be used in combination with one or more features of another of the examples, or a combination of other examples. Furthermore, equivalents and modifications not described above may also be employed without departing from the scope of the invention, which is defined in the accompanying claims. In the claims, the word "comprising" does not exclude other elements or operations, and the indefinite article "a" or "an" does not exclude a plurality. The mere fact that certain features are recited in mutually different dependent claims does not indicate that a combination of these features cannot be used to advantage. Any reference signs in the claims should not be construed as limiting their scope.

The invention claimed is:

1. A computer-implemented method of predicting a status of an embolization procedure on an aneurism, the method comprising:

receiving projection image data representing temporal blood flow in a region of the anatomy including the aneurism during the embolization procedure;

predicting temporal blood flow during the embolization procedure based on the projection data and a representation of temporal blood flow in a region of the anatomy that does not include an aneurism; and generating an output indicative of the status of the embolization procedure based on the predicted blood flow.

2. The computer-implemented method according to claim 1, further comprising computing a value of an out-of-distribution metric indicative of the predicted temporal blood flow relative to a normal blood flow; and wherein the generating the output indicative of the status of the embolization procedure, is based on the computed value of the out-of-distribution metric.

3. The computer-implemented method according to claim 2, wherein the projection image data is input into a neural network trained to predict the temporal blood flow during the embolization procedure, wherein the neural network is trained using training data representing the temporal blood flow in the region of the anatomy that does not include the aneurism; and one of:

i) the neural network is configured to generate a reconstruction error value representing a difference between the predicted temporal blood flow and the blood flow represented in the inputted projection image data and/or a divergence value representing a difference between the probability distribution of the latent representation of the inputted projection image data and a reference probability distribution; and wherein the value of the out-of-distribution metric is computed based on the reconstruction error value and/or the divergence value; or ii) the neural network is configured to generate an attention map indicating a position of one or more features in the inputted projection image data having a dominant contribution to the predicted temporal blood flow; and wherein the value of the out-of-distribution metric is computed based on a difference between the position of the one or more features indicated in the attention map, and a position of the aneurism in the inputted projection image data.

4. The computer-implemented method according to claim 1, wherein the projection image data comprises a sequence of X-ray images.

5. The computer-implemented method according to claim 1, wherein the projection image data includes a representation of the temporal blood flow in one or more lumens upstream of the aneurism, and in one or more lumens downstream of the aneurism.

6. The computer-implemented method according to claim 1, wherein the status of the embolization procedure represents one or more of:

i) a proportion of the embolization procedure that has been completed; and ii) an expected time to complete the embolization procedure.

7. The computer-implemented method according to claim 1, further comprising generating an output indicative of an expected clinical outcome of the embolization procedure at a future point in time.

8. The computer-implemented method according to claim 1, further comprising identifying the aneurism in the received projection image data prior to inputting the received projection image data into a neural network trained to predict the temporal blood flow during the embolization procedure, wherein the neural network is trained using training data representing the temporal blood flow in the region of the anatomy that does not include the aneurism.

9. The computer-implemented method according to claim 8, wherein the identifying the aneurism comprises:

i) receiving user input indicative of a region of interest in the received projection image data that includes the aneurism; or ii) automatically identifying the aneurism in the received projection image data.

10. The computer-implemented method according to claim 1, wherein a neural network is trained to predict the status of the embolization procedure based on patient data and the received projection image data, and wherein the method further comprises:

receiving patient data relating to the aneurism;

inputting the received patient data and the received projection image data into the neural network; and predicting, by the neural network, the status of the embolization procedure based on the received patient data and the received projection image data.

11. The computer-implemented method according to claim 10, wherein the neural network comprises one or more of the following architectures: variational auto-encoder, recurrent neural network, long short term memory.

12. The computer-implemented method according to claim 11, wherein the neural network comprises a variational auto encoder architecture and wherein the neural network is trained to learn one or more vectors of latent variables representing a distribution of blood flow, and wherein the neural network is trained to predict the temporal blood flow based on the learned one or more vectors of latent variables.

13. The computer-implemented method according to claim 11, wherein the neural network is trained to learn the one or more vectors of latent variables representing a distribution of blood flow by:

receiving training data comprising a plurality of temporal sequences of images, each temporal sequence including images representing blood flow at a plurality of time steps in a region of the anatomy that does not include an aneurism; and for each of a plurality of time steps in a temporal sequence:

inputting into the neural network, the image corresponding to the time step;

training the neural network to learn the one or more vectors of latent variables representing the distribution of blood flow in the image at the time step;

sampling from within the distribution of blood flow in the image represented by the one or more vectors of latent variables to provide an expected blood flow at a subsequent time step;

adjusting parameters of the neural network based on:

i) a value of a first loss function representing a difference between the probability distribution of the one or more vectors of latent variables, and a reference probability distribution; and ii) a value of a second loss function representing a difference between the predicted blood flow in the image at the subsequent time step, and the blood flow in the input image from the training data representing the blood flow at the subsequent time step, until a stopping criterion is met; and repeating the inputting, the training, the sampling and the adjusting for each temporal sequence of images.

14. The computer-implemented method according to claim 1, further comprising:

receiving volumetric image data corresponding to the region of the anatomy in the received projection image data, the volumetric image data being generated prior to commencement of the embolization procedure;

simulating, based on a segmentation of the volumetric image data, a blood flow in the region of the anatomy in the absence of the aneurism; and wherein the generating an output indicative of the status of the embolization procedure, is determined based further on a comparison between the simulated blood flow in the region of the anatomy in the absence of the aneurism, and the predicted temporal blood flow predicted by the neural network.

15. A non-transitory computer-readable storage medium having stored a computer program comprising instructions which, when executed by one or more processors, cause the one or more processors to:

receive projection image data representing temporal blood flow in a region of the anatomy including the aneurism during the embolization procedure;

predict temporal blood flow during the embolization procedure based on the projection data and a representation of temporal blood flow in a region of the anatomy that does not include an aneurism; and generate an output indicative of the status of the embolization procedure based on the predicted blood flow.

16. The non-transitory computer-readable storage medium according to claim 15, wherein the projection image data is input into a neural network trained to predict the temporal blood flow during the embolization procedure, wherein the neural network is trained using training data representing the temporal blood flow in the region of the anatomy that does not include the aneurism.

* * * * *